(12) United States Patent
Farnan et al.

(10) Patent No.: US 10,342,913 B2
(45) Date of Patent: Jul. 9, 2019

(54) CANNULA LINED WITH TISSUE IN-GROWTH MATERIAL

(71) Applicant: CircuLite, Inc., Teaneck, NJ (US)

(72) Inventors: Robert C. Farnan, Fort Lauderdale, FL (US); Oliver Marseille, Aachen (DE)

(73) Assignee: CircuLite, Inc., Teaneck, NJ (US)

( * ) Notice: Subject to any disclaimer, the term of this patent is extended or adjusted under 35 U.S.C. 154(b) by 0 days.

(21) Appl. No.: 15/695,145

(22) Filed: Sep. 5, 2017

(65) Prior Publication Data
US 2018/0008765 A1   Jan. 11, 2018

Related U.S. Application Data

(63) Continuation of application No. 13/204,201, filed on Aug. 5, 2011, now Pat. No. 9,750,866, which is a continuation-in-part of application No. 13/025,845, filed on Feb. 11, 2011, now Pat. No. 9,504,776.

(60) Provisional application No. 61/303,351, filed on Feb. 11, 2010.

(51) Int. Cl.
| | |
|---|---|
| *A61N 1/362* | (2006.01) |
| *A61M 1/36* | (2006.01) |
| *A61M 1/10* | (2006.01) |
| *A61B 17/00* | (2006.01) |
| *A61M 1/12* | (2006.01) |
| *A61M 25/02* | (2006.01) |

(52) U.S. Cl.
CPC .......... *A61M 1/3653* (2013.01); *A61M 1/101* (2013.01); *A61M 1/1008* (2014.02); *A61M 1/3659* (2014.02); *A61B 2017/00252* (2013.01); *A61M 1/12* (2013.01); *A61M 2025/0293* (2013.01)

(58) Field of Classification Search
CPC .. A61M 1/3653; A61M 1/1008; A61M 1/101; A61M 1/12; A61M 2025/0293; A61N 1/3659; A61B 2017/00252
See application file for complete search history.

(56) References Cited

U.S. PATENT DOCUMENTS

| | | | |
|---|---|---|---|
| 3,843,974 A * | 10/1974 | Miller | .................... A61L 27/14 428/336 |
| 4,086,665 A | 5/1978 | Poirier | |
| 6,050,975 A | 4/2000 | Poirier | |
| 2006/0235357 A1 | 10/2006 | Woodward et al. | |
| 2007/0197855 A1 * | 8/2007 | Richardson | ......... A61M 1/3653 600/16 |

(Continued)

FOREIGN PATENT DOCUMENTS

WO        9520984 A2    8/1995

OTHER PUBLICATIONS

European Patent Office, Supplementary European Search Report in EP Application No. 11742879, dated Aug. 29, 2017.

*Primary Examiner* — Lindsey G Wehrheim
(74) *Attorney, Agent, or Firm* — Christopher & Weisberg, P.A.

(57) ABSTRACT

A cannula for moving fluids between a pump and the circulatory system of a patient. The cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A jacket surrounds at least part of the liner.

21 Claims, 13 Drawing Sheets

(56) References Cited

U.S. PATENT DOCUMENTS

2010/0016928 A1\* 1/2010 Zdeblick .................. A61N 1/05
607/72

\* cited by examiner

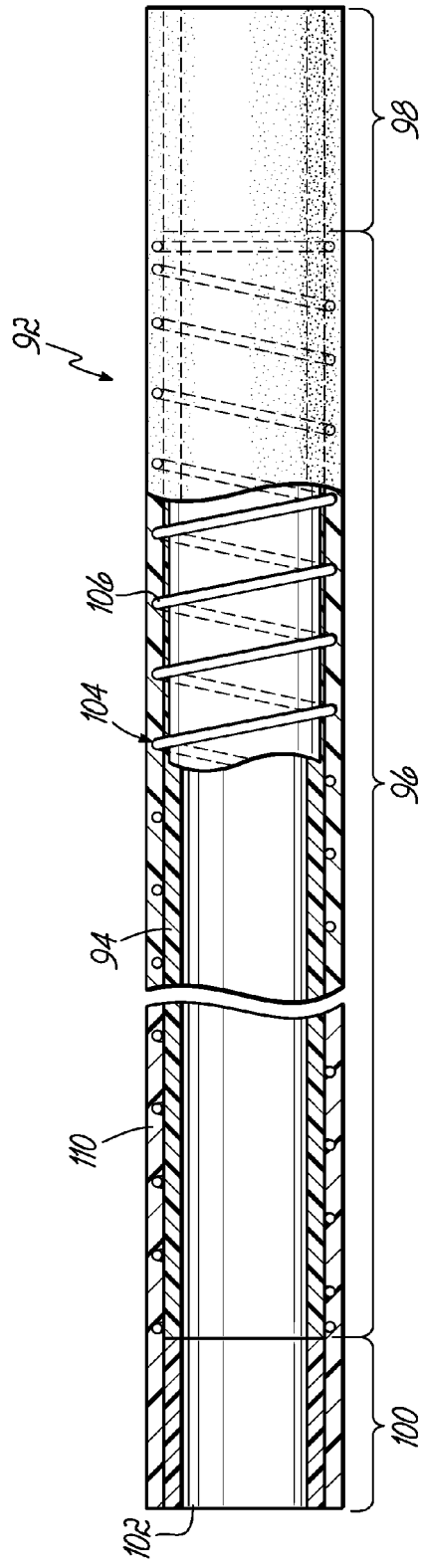
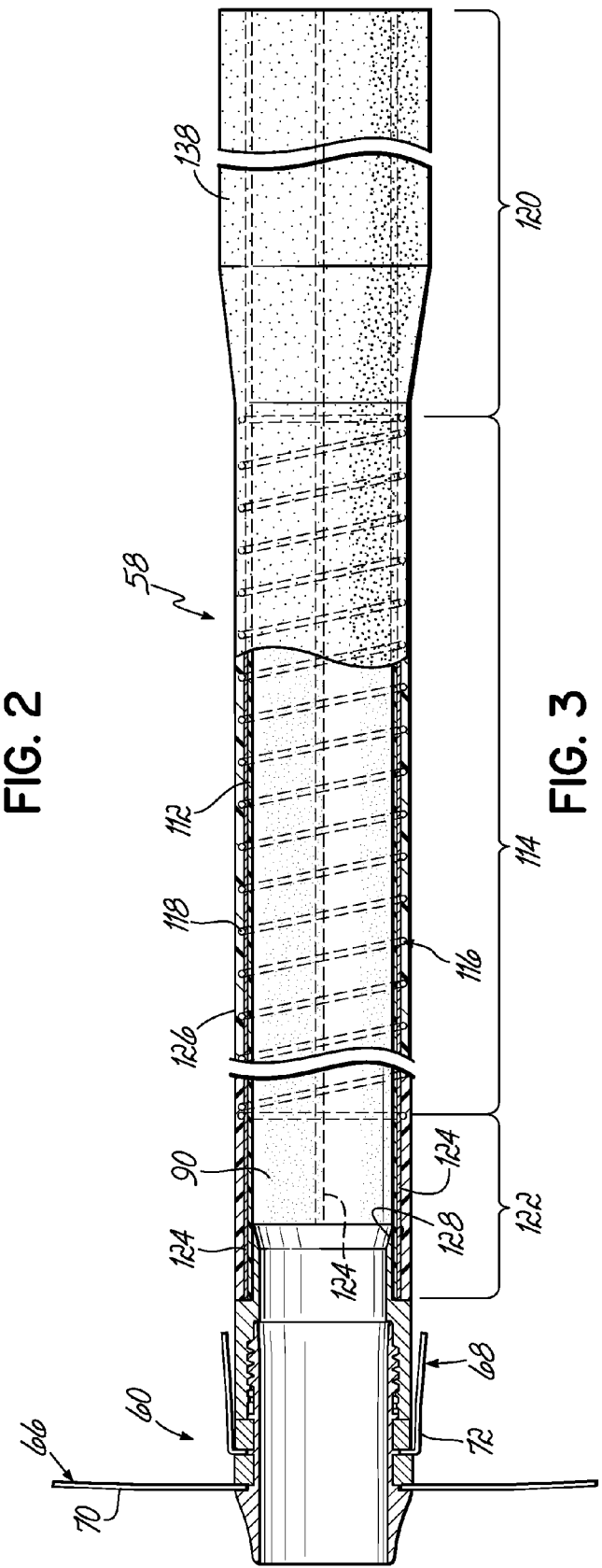
FIG. 2
FIG. 3

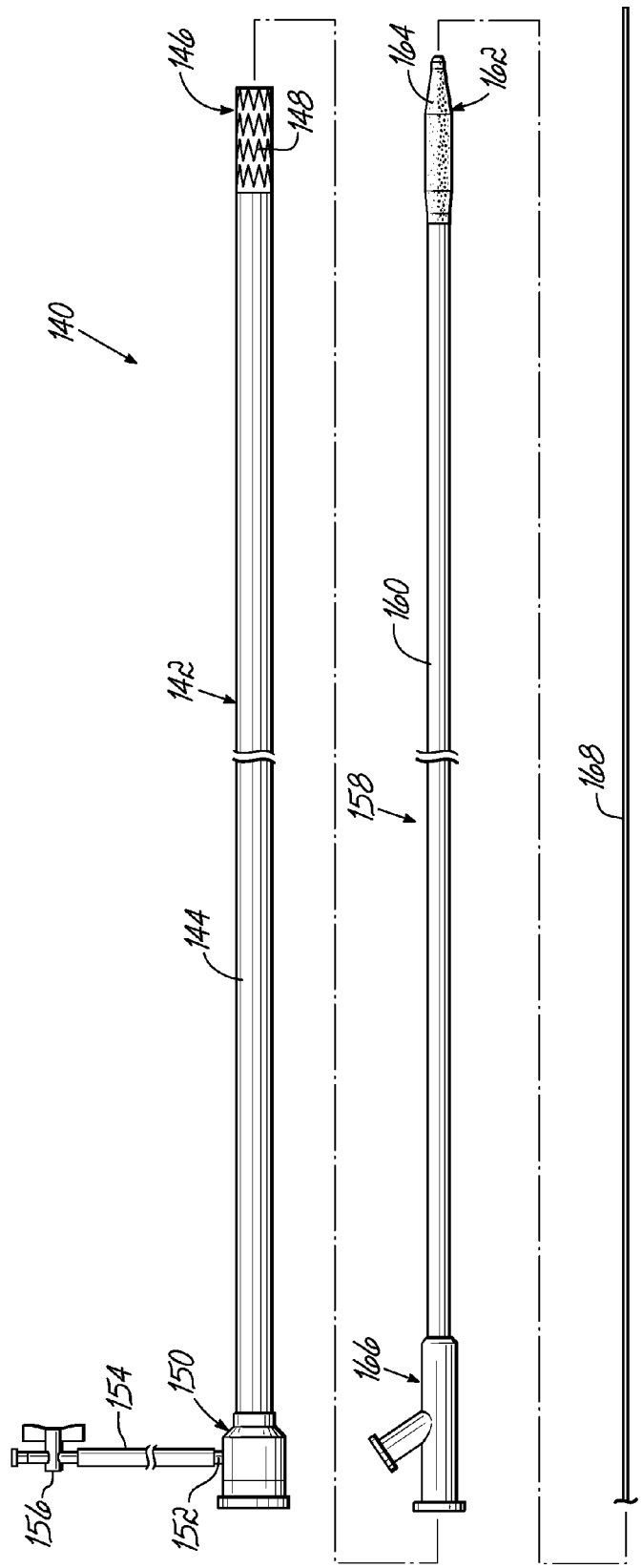
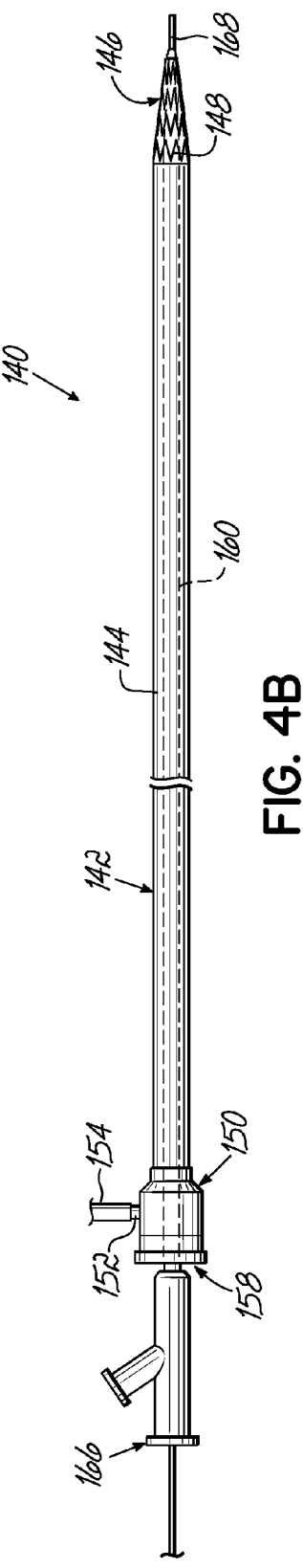
FIG. 4A
FIG. 4B

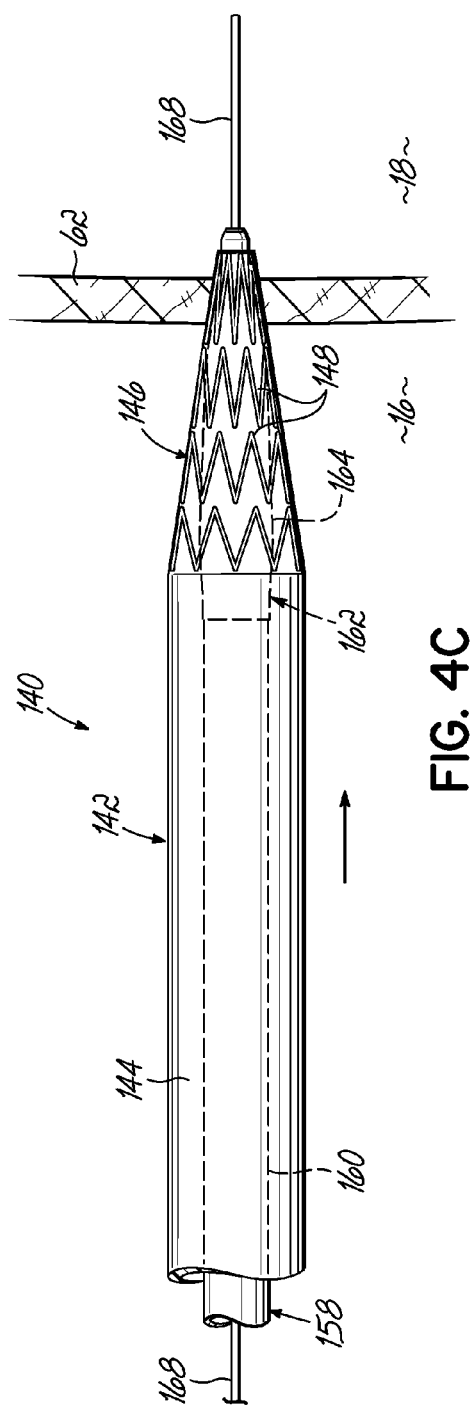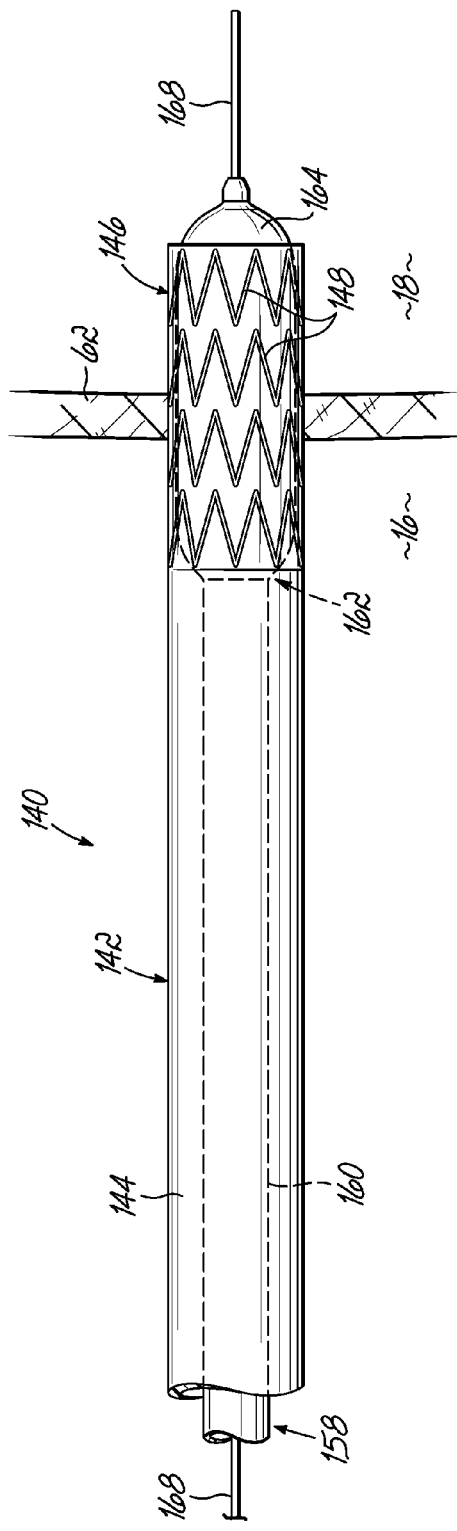
FIG. 4C
FIG. 4D

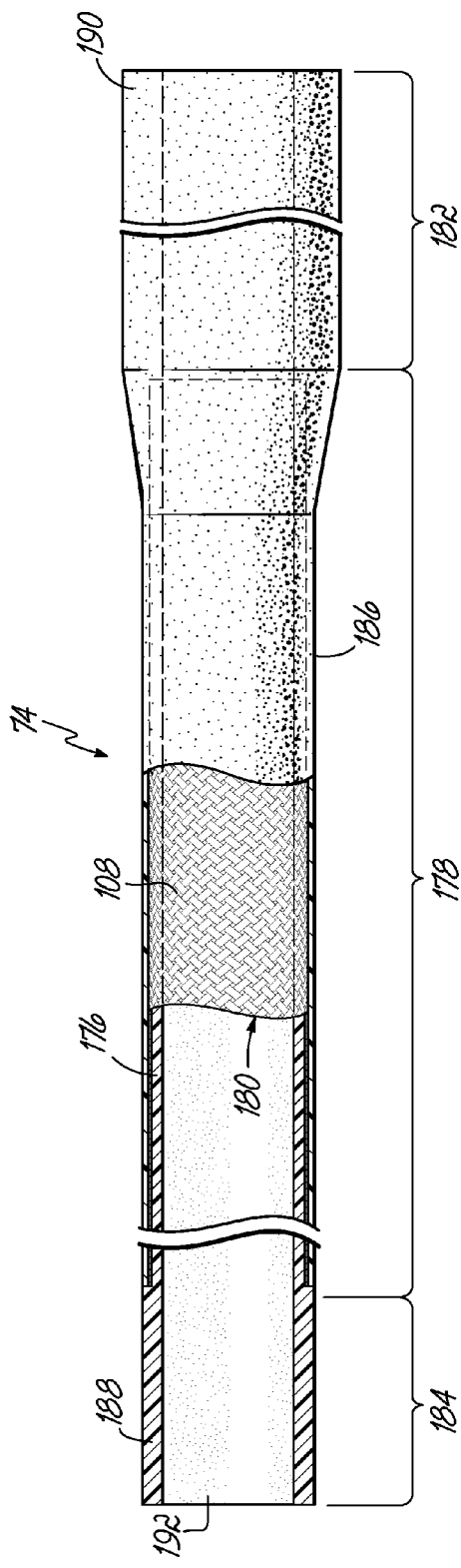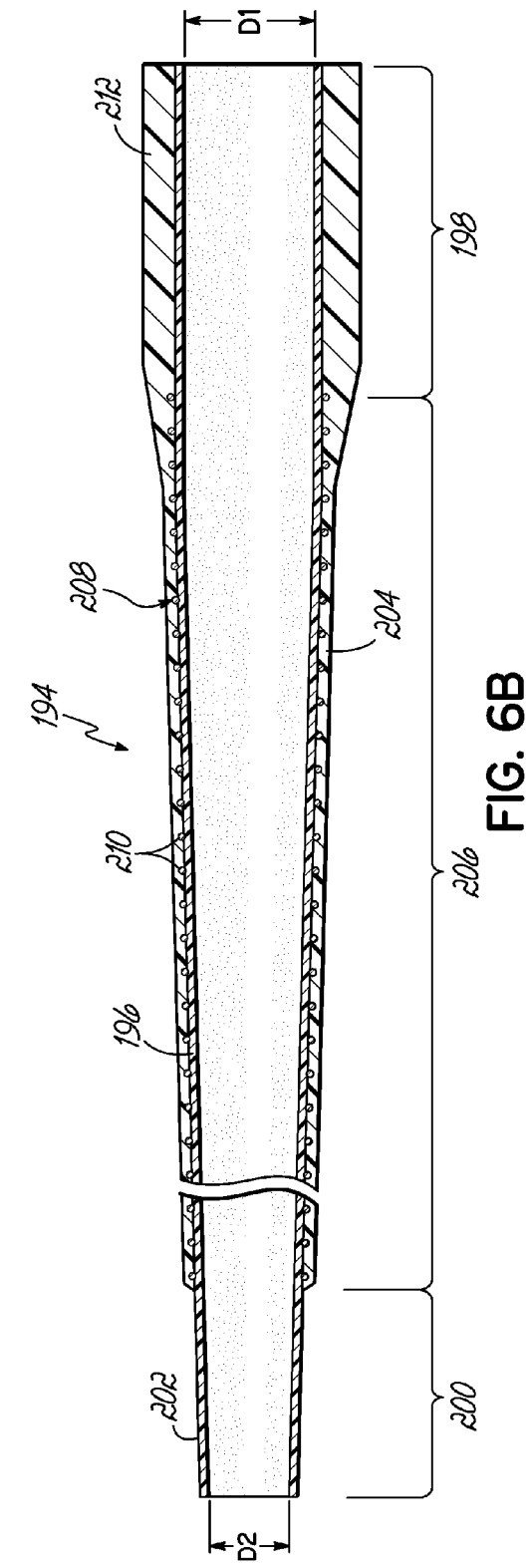

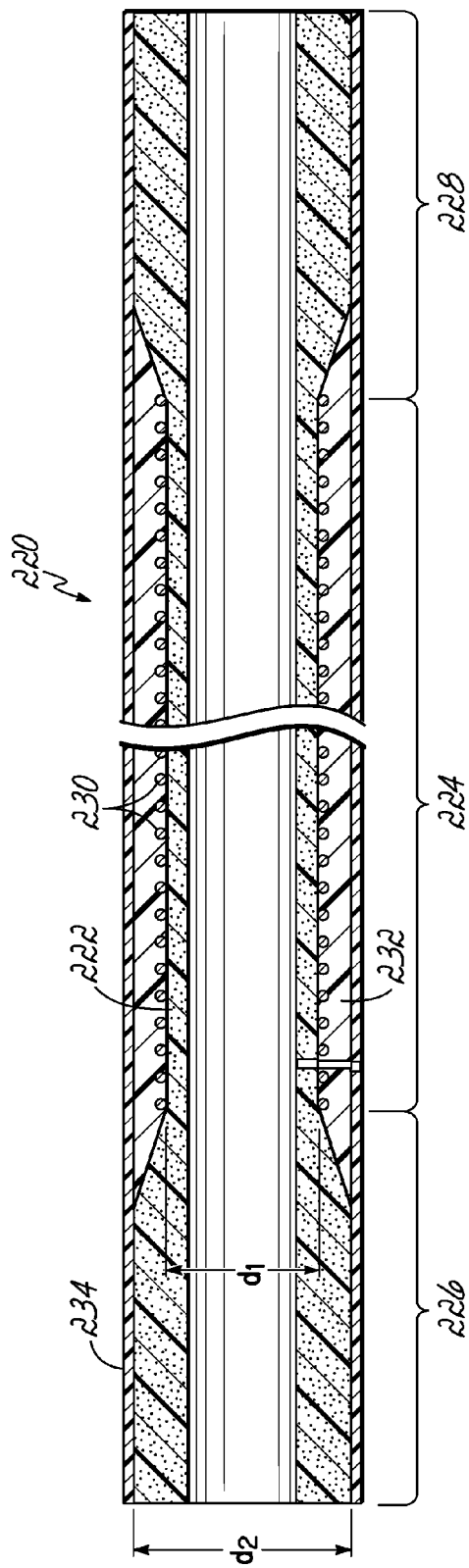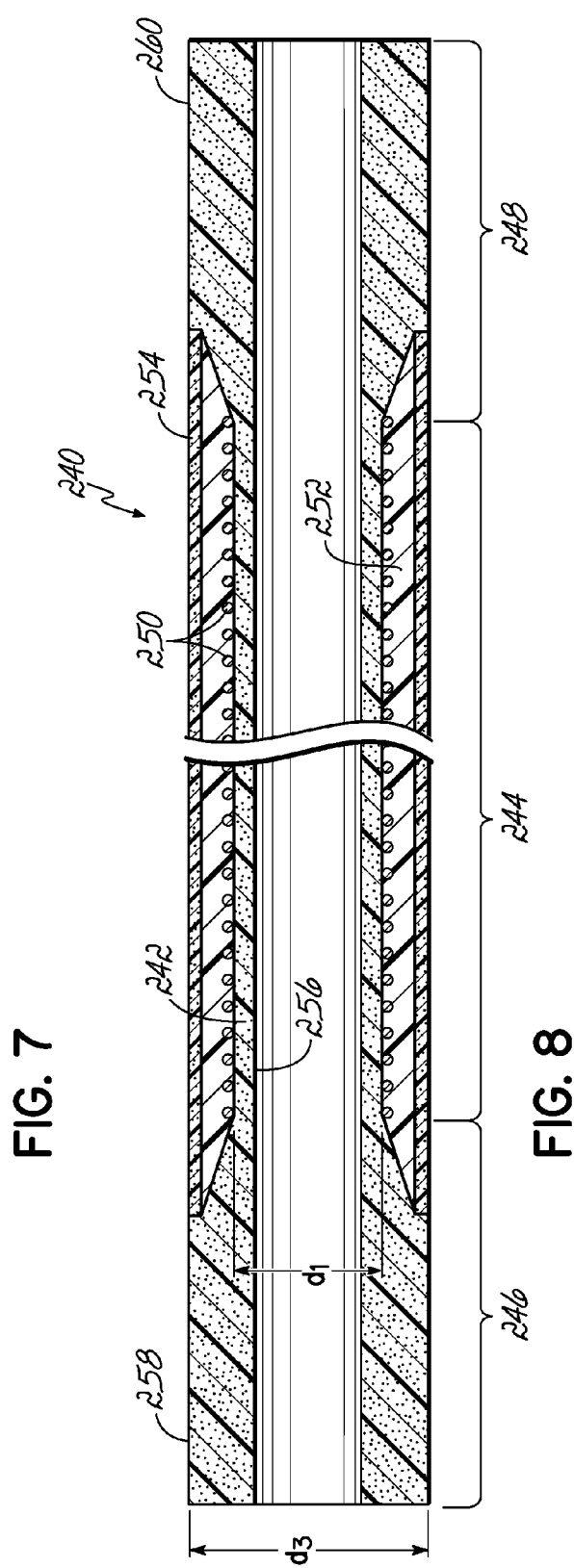

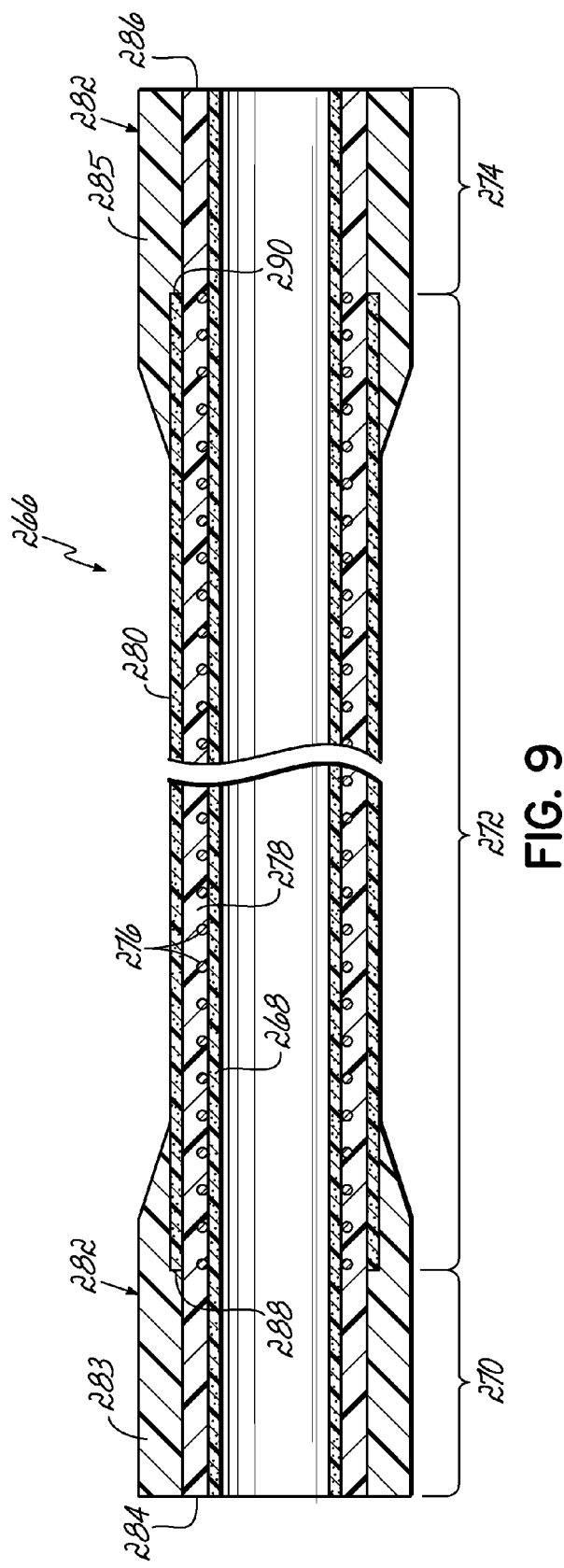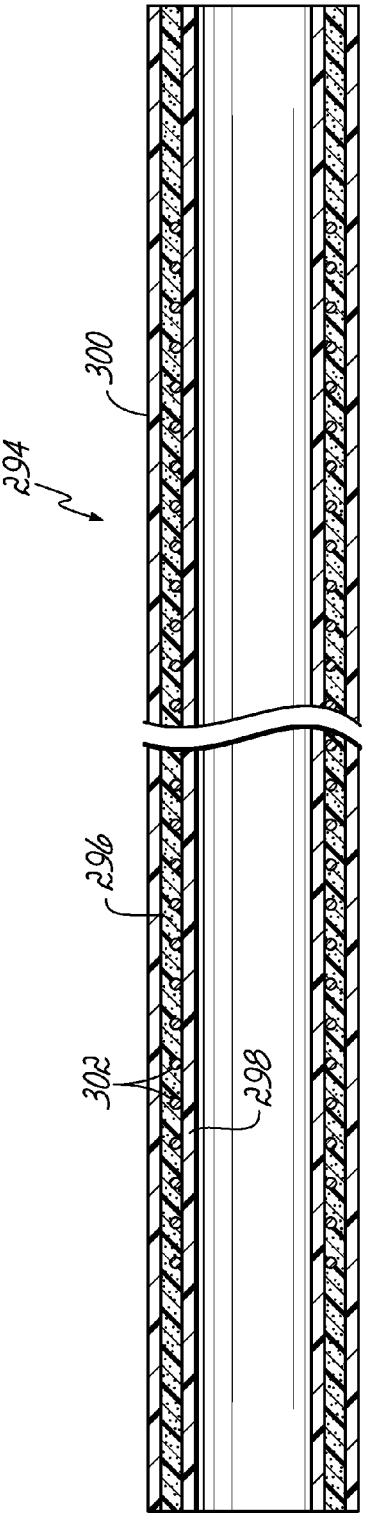

CANNULA LINED WITH TISSUE IN-GROWTH MATERIAL

CROSS-REFERENCE TO RELATED APPLICATION

This application is a continuation of U.S. patent application Ser. No. 13/204,201, filed Aug. 5, 2011 (pending), which is a continuation-in-part of U.S. patent application Ser. No. 13/025,845, filed on Feb. 11, 2011 (now U.S. Pat. No. 9,504,776), which claims the benefit of U.S. Provisional Patent Application Ser. No. 61/303,351, filed on Feb. 11, 2010, the disclosures of which are incorporated by reference herein, in their entirety.

TECHNICAL FIELD

The present invention relates generally to cannulae, and more specifically to cannulae for use with the pump of a circulatory assist system.

BACKGROUND

The human heart is the muscle that is responsible for pumping blood throughout the vascular network. Veins are vessels that carry blood toward the heart while arteries carry blood away from the heart. The human heart consists of two atrial chambers and two ventricular chambers. Atrial chambers receive blood from the body and the ventricular chambers, which include larger muscular walls, pump blood from the heart. A septum separates the left and the right sides of the heart.

Various devices and methods have been utilized to assist the heart in blood circulation, particularly for patients having congestive heart failure (commonly referred to as heart disease), which is a condition that results in any structural or functional cardiac disorder that impairs the ability of the heart to fill with or pump blood throughout the body. These devices generally include a pump, which may reside in a subcutaneous pump pocket, and cannulae fluidically attaching the pump to the vascular network. One cannula is used to transmit oxygenated blood from the left side of the heart to the pump; another cannula is used to direct that blood from the pump to the arterial network.

Despite the benefits gained by assisting the heart with the implantable pump, issues may arise from the presence of the cannula within the vessel. The arteries and veins of the vascular network have a particular anatomical structure that includes three layers: the tunica externa, the tunica media, and the tunica intima, respectively from the outer most layer, inward. The tunica intima, which includes a combination of endothelial cells and the protein elastin, creates a biological barrier that performs several functions. One essential function is the maintenance of a smooth inner surface that resists clotting and promotes smooth blood flow. The endothelial cells secrete various regulatory compounds that aid processes, such as vasoregulation and coagulation. When a conventional cannula is positioned within a blood vessel, the polymer or urethane comprising the cannula, or the mere presence of the cannula itself, may physically and/or chemically perturb the endothelial cells of the tunica intima and induce a prothrombotic environment. Thrombus formations may wash into the implantable pump of the assist device causing pump failure or alternatively induce a thrombolic event, including stroke or kidney infarct. Accordingly, it would be beneficial to create an environment within the cannula that mimics the native biological structure and framework of the blood vessel to reduce the occurrence of thrombic events.

SUMMARY

In one illustrative embodiment, the invention is directed to a cannula for moving fluids between a pump and the circulatory system of a patient. The cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A jacket surrounds at least part of the liner.

In another illustrative embodiment, the invention is directed to a cannula for moving fluids between a pump and the circulatory system of a patient. The cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A reinforcing structure surrounds at least a part of the intermediate portion for resisting kinks along the length of the cannula. A jacket surrounds the reinforcing structure and at least part of the liner.

According to another illustrative embodiment, the invention is directed to an inflow cannula for moving fluids between the heart of a patient and a pump. The inflow cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A tip is coupled to the distal portion of the inflow cannula for securing the inflow cannula to a wall of the heart. A hub of the inflow cannula is coupled to the proximal portion of the inflow cannula and secures the inflow cannula to the pump.

In accordance with yet another illustrative embodiment, the invention is directed to an outflow cannula for moving fluids between a pump and an arterial structure of the circulatory system of a patient. The outflow cannula includes a liner having an intermediate portion between a proximal portion and a distal portion, and a lumen extending between the proximal and distal portions. At least the intermediate portion of the liner is constructed from a tissue in-growth material for supporting the growth of endothelial cells. A hub is coupled to the proximal portion of the outflow cannula for securing the outflow cannula to the pump. A distal end of the outflow cannula is configured to be coupled to the arterial structure.

A cannula delivery system is described in accordance with another illustrative embodiment of the invention. The cannula delivery system includes a delivery sheath and a dilator. The delivery sheath has a body with proximal and distal ends and a lumen extending between. The distal end of the body includes a balloon-expandable section having two states: a first state with a smaller diameter and a second state with a larger diameter. In the second state, the balloon-expandable section is configured to receive a cannula and to move relative thereto. The dilator has a distally-positioned inflation member that is positioned within the balloon-expandable section of the delivery sheath. Inflation of the distally-positioned inflation member expands the balloon-expandable section from its first state to its second state.

Another illustrative embodiment of the invention is directed to a method of percutaneously inserting a cannula into a tissue. The method includes directing a delivery sheath through a puncture in the tissue. The delivery sheath has a body with proximal and distal ends and a lumen extending between. The distal end of the body includes a balloon-expandable section in a first, collapsed state. An inflation member positioned within the balloon-expandable section is inflated and causes expansion of the balloon-expandable section from the first, collapsed state to a second, expanded state. This dilates the puncture in the tissue. The inflation member is deflated and retracted from the delivery sheath so that a cannula may be directed into and through the lumen of the delivery sheath to the balloon-expandable section. The delivery sheath is retracted, relative to the cannula, which extends through the dilated puncture.

In another illustrative embodiment, the invention is directed to a cannula assembly that includes a flexible cannula body, a tip, an anchor, and a porous polymeric structure. The tip is coupled to a distal portion of the flexible cannula body and the anchor is coupled to the tip. The anchor is configured to be deployed from a contracted state to an expanded state. In the expanded state, the anchor engages at least one side of the heart tissue and resists movement of the cannula in at least one direction. The porous polymeric structure is coupled to an outer surface of the tip, adjacent to the anchor, and is configured to facilitate tissue in-growth.

According to another embodiment of the invention, a cannula is described. The cannula includes a liner and a jacket, each being constructed from a polymer material. An intermediate layer resides between the liner and the jacket and is constructed from a porous material.

BRIEF DESCRIPTION OF THE DRAWINGS

FIG. 2 is a side-elevational view of one exemplary embodiment of a cannula, shown in partial cross-section.

FIG. 3 is a side-elevational view of one exemplary embodiment of an inflow cannula for use with the circulatory assist system, shown in partial cross-section.

FIG. 4A is a disassembled, side-elevational view of an exemplary embodiment of a cannula delivery system and including a delivery sheath, a dilator, and a guide-wire.

FIG. 4B is an assembled, side-elevational view of the cannula delivery system of FIG. 4A, shown in a collapsed state.

FIGS. 4C-4E are enlarged, side-elevational views of an exemplary method of advancing the assembled cannula delivery system of FIG. 4B across a tissue wall.

FIG. 6A is a side-elevational view of one exemplary embodiment of an outflow cannula for use with the circulatory assist system, shown in partial cross-section.

FIG. 6B is a cross-sectional view of an alternative embodiment of an outflow cannula for use with the circulatory assist system, shown in partial cross-section.

FIG. 7 is a cross-sectional view of a cannula in accordance with another embodiment of the invention, shown in cross-section.

FIG. 8 is a cross-sectional view of yet another cannula in accordance with another embodiment of the invention, shown in cross-section.

FIG. 9 is a cross-sectional view of a cannula in accordance with another embodiment of the invention, shown in cross-section.

FIG. 10 is a cross-sectional view of a cannula in accordance with another embodiment of the invention, shown in cross-section.

DETAILED DESCRIPTION

Figure 1:
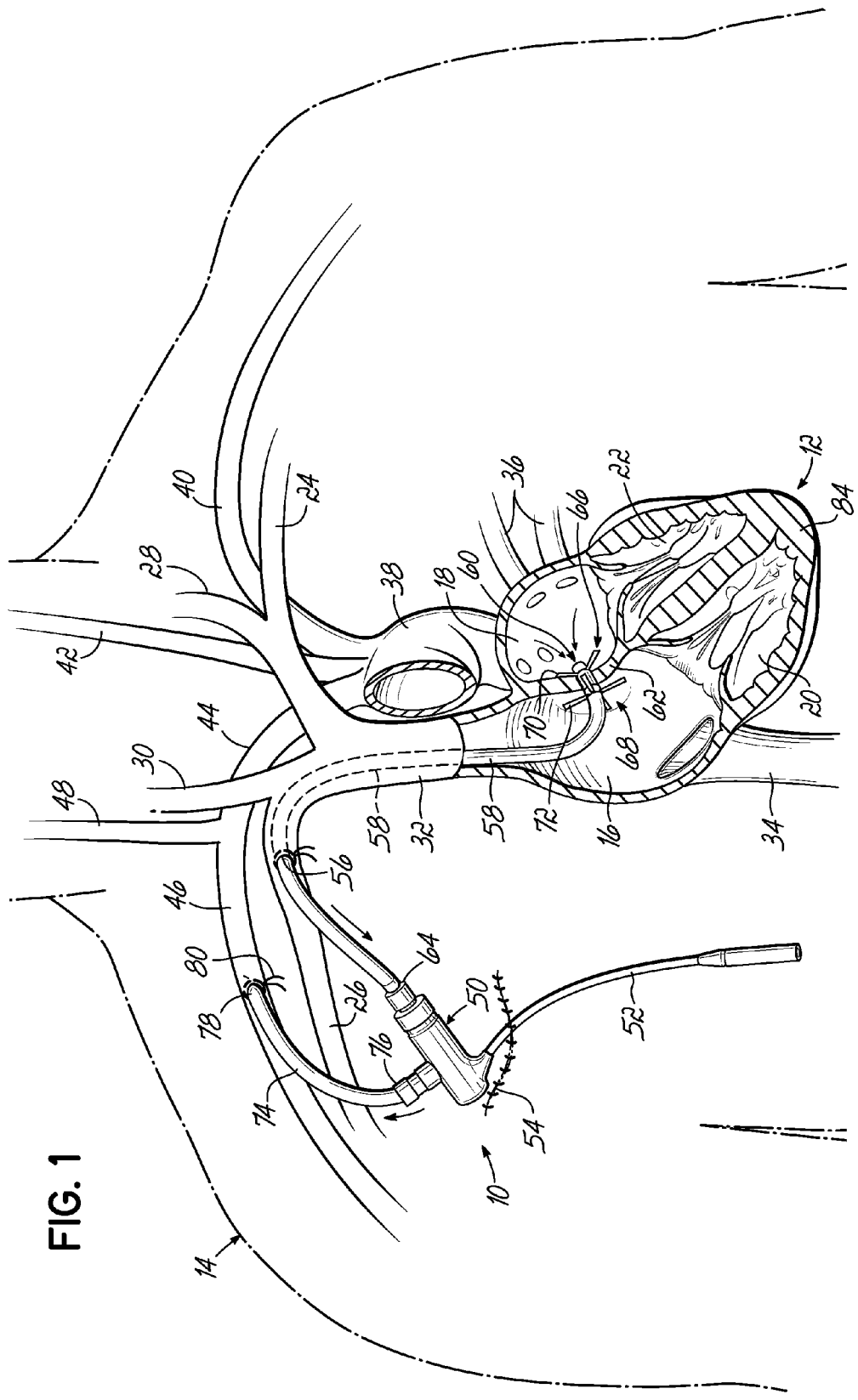
FIG. 1 is a diagrammatic view of a circulatory assist system, with the heart shown in cross-section.

FIG. 1 illustrates an implanted circulatory assist system 10. For illustrative purposes, certain anatomy is shown including the heart 12 of a patient 14 having a right atrium 16, a left atrium 18, a right ventricle 20, and a left ventricle 22. Blood from the left and right subclavian veins 24, 26 and the left and right jugular veins 28, 30 enters the right atrium 16 through the superior vena cava 32 while blood from the lower parts of the body enters the right atrium 16 through the inferior vena cava 34. The blood is pumped from the right atrium 16, to the right ventricle 20, and to the lungs (not shown) to be oxygenated. Blood returning from the lungs enters the left atrium 18 via pulmonary veins 36 and is then pumped into the left ventricle 22. Blood leaving the left ventricle 22 enters the aorta 38 and flows into the left subclavian artery 40, the left common carotid 42, and the brachiocephalic trunk 44 including the right subclavian artery 46 and the right common carotid 48.

With respect to the implanted circulatory assist system 10, two cannulae extend between the vascular network and a pump 50, which may be any implantable or extracorporeal pump that may be radially- and/or axially-driven. Those skilled in this art, however, recognize that other types of pumps may be used in other embodiments but may include pumps such as those described in U.S. patent application Ser. No. 11/627,444, published as 2007/0197854, which is incorporated herein by reference in its entirety.

A cable 52 may extend transdermally from the pump 50 to a position in the abdomen where the cable 52 exits the patient 14 and connects to a power supply (not shown). Suitable power supplies may be any universal-type power supply that sends power to the pump 50 via the cable 52 and may include, but is not limited to, a rechargeable battery pack.

As illustrated, the physician may position the implantable pump 50 at least subcutaneously and, optionally, submuscularly in a pump pocket 54 located near a venous access site 56, or alternatively, maintain the pump 50 externally.

A first, inflow cannula 58 extends from a tip 60 within the left atrium 18, across the intra-atrial septum 62, and percutaneously to the venous access site 56, shown here to be in the right subclavian vein 26. The inflow cannula 58 extends through the venous access site 56 to an input port 64 of the pump 50. Though not shown, the inflow cannula 58 may alternatively be surgically connected to either the left or right side of the heart 12 (for example, surgically coupled to the left or right atria 18, 16) and extend to the pump 50 through the thoracic cavity in a manner described generally in U.S. patent application Ser. No. 11/846,839, published as 2008/0076959, the disclosure of which is incorporated herein in its entirety. The tip 60 may have various shapes, including those described in U.S. patent application Ser. No. 12/392,623 (published as 2009/0182188) and Ser. No. 12/256,911 (published as 2009/0112050), the disclosures of which are also incorporated herein by reference in their entireties. In any event, the illustrative tip 60 includes first and second deployable anchors 66, 68, each including a plurality of struts 70, 72, respectively, for securing the tip 60 to the intra-atrial septum 62.

The struts 70, 72 of the anchors 66, 68 of the tip 60 may be constructed by chemically etching the structure from a sheet of a superelastic material, electropolishing the etched structure to remove rough edges generated during the formation process, and then heating the structure to a superelastic state. Because of the superelastic state, the anchors 66, 68 may be deployable from a folded position (see the second anchor 68 in FIG. 3) to a deployed position that extends radially from the tip 60 (see the first anchor 66 in FIG. 3). It would be readily appreciated that while four struts 70, 72 per anchor 66, 68 are shown, any number of struts may be used.

In some embodiments, though not specifically shown, the struts 70, 72 may be encapsulated within a porous polymeric structure that provides a larger surface for engaging the tissue of the vascular structure than the plurality of struts 70, 72 alone when the tip 60 is inserted into the vascular structure. Additionally, the porous polymeric structure allows for tissue in-growth, wherein tissue from the wall of the vascular structure may grow and embed within the porous polymeric structure to provide greater structural stability and sealing capacity. Further details of the first and second anchors 66, 68 may be found in U.S. patent application Ser. No. 12/256,911.

A second, outflow cannula 74 extends from an output port 76 of the pump 50 to an arterial access site 78, illustrated here in the right subclavian artery 46. The outflow cannula 74 may be secured at the arterial access site 78 by one or more sutures 80 or one or more anastomotic connectors (not shown), such as those taught in U.S. patent application Ser. No. 12/829,425, the disclosure of which is incorporated herein by reference, in its entirety.

Alternatively, the physician may surgically position the inflow cannula 58 in accordance with another embodiment and such that the tip 82 extends through the apex 84 of the heart 12 and into the left ventricle 22. The tip 82, which is described in greater detail in U.S. patent application Ser. No. 13/025,757, the disclosure of which is incorporated herein by reference in its entirety. The tip includes one or more openings 86 that extend proximally from a distal tip end 88. The openings 86 permit the flow of blood from the left ventricle 22 into a lumen 90 (FIG. 3) of the inflow cannula 58 even in the event that the distal tip end 88 becomes obstructed with tissue from within the left ventricle 22. Inclusion of this particular embodiment of the tip 82 is not required, but instead may be replaced with other tips that are suitable for insertion through the apex 84. The outflow cannula 74 may extend from the pump 50 to an arterial access site 78', for example, within the ascending aorta 38. Other arrangements, though not shown, may also be used in accordance with the particular need and to accommodate the unique anatomy of the patient 14.

Figure 1A:
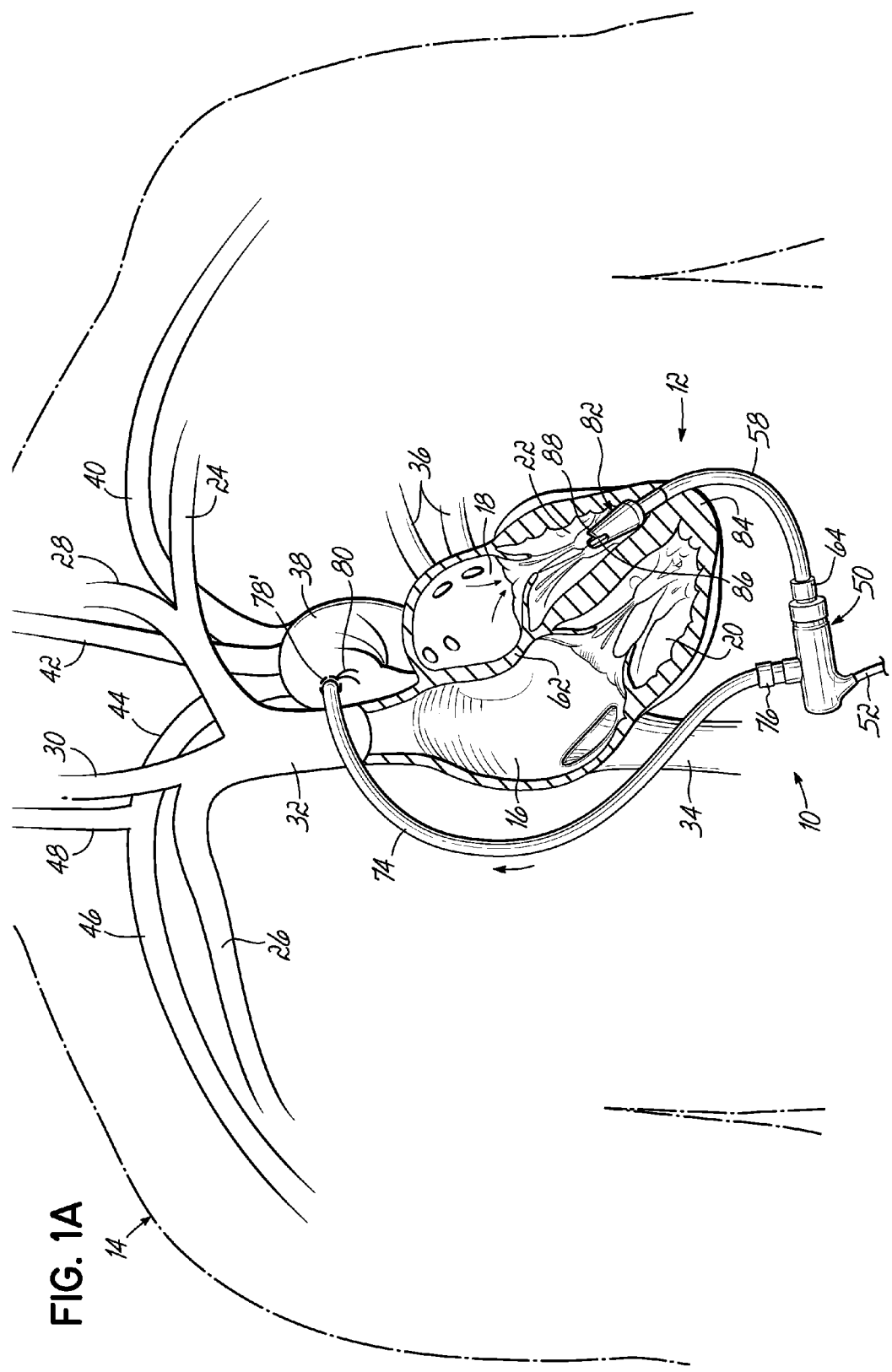
FIG. 1A is a diagrammatic view of an alternate position of the circulatory assist system, with the heart shown in cross-section.

Use of known, conventional cannula with the circulatory assist system 10 of FIGS. 1 and 1A may induce a prothrombotic environment. Therefore, the inflow cannula 58 or the outflow cannula 74 or both may be constructed in a manner that mimics the native biological structure and framework of blood vessels. Accordingly, and with reference now to FIG. 2, one such biocompatible cannula 92 structure is described in greater detail.

The biocompatible cannula 92 includes a liner 94 having an intermediate portion 96 between a proximal portion 98 and a distal portion 100, with a lumen 102 extending therethrough. In some embodiments, the portions 96, 98, 100 of the liner 94 are constructed as a unitary structure that extends the full length of the biocompatible cannula 92. Alternatively, a majority of the length of the liner 94, i.e., the intermediate portion 96, is constructed from a tissue in-growth material while the proximal and distal portions 98, 100 include other materials as described below. The tissue in-growth material may be a porous polymeric material, such as expanded polytetrafluoroethylene (ePTFE), a woven polyester fabric tubing (e.g., DACRON brand of polyester fabric), velour, or like materials that create a scaffolding to which endothelial cells adhere and create a biostable environment within the cannula 92 in a manner described in greater detail below. Alternatively, the proximal and distal portions 98, 100 are constructed from a polymeric material and are added to the respective ends of the intermediate portion 96. Suitable polymeric materials for the proximal and distal portions 98, 100 may include elastomeric materials, such as polyurethanes or silicones, that are capable of connecting the cannula 92 to the pump 50 (FIG. 1) or to a distally-positioned cannula tip 60 (FIG. 1).

One or more portions of the liner 94 may be surrounded by a reinforcing structure 104 to resist the collapse or kinking of the cannula 92 while providing the desired level of flexibility; however, the reinforcing structure 104 would generally not extend to the proximal and distal portions 98, 100 so that these portions may remain flexible, i.e., radially expandable, for extending over and attaching to the tip 60 (FIG. 1) or the pump 50 (FIG. 1), as appropriate. The reinforcing structure 104 may be constructed as a coil 106 (shown) or a braid 108 (FIG. 6A) from metallic materials, such as stainless steel, chromium cobalt, or nickel titanium, or from a rigid polymeric material.

The liner 94 and the reinforcing structure 104 are covered with a jacket 110, which may be constructed from a polymeric material. With a heat melt process, the liner 94 bonds to the polymeric material of the jacket 110 and encapsulates the reinforcing structure 104. In some embodiments, an outer surface of the liner 94 may be coated with a thin layer of solution grade polyurethane or a silicone. This low viscosity coating facilitates the introduction of the polymeric material of the jacket 110 into the structure of the porous polymeric material of the liner 94. For urethane-based constructions, the bonding between the liner 94 and the jacket 110 occurs through a melt process; for silicone-based constructions, the bonding between the liner 94 and the jacket 110 occurs through a cross-linking process during the curing cycle of construction. The proximal end of the jacket 110 may be structured as desired to accommodate the coupling of the cannula 92 to the pump 50 (FIG. 1). This may include a flared or expanded section to form a hub and is described in greater detail below with reference to FIGS. 3 and 5A.

It would be understood that in those embodiments where the liner 94 is constructed as a unitary structure, the jacket 110 would bond directly to the tissue in-growth material of the liner 94.

FIG. 3 illustrates the inflow cannula 58 of FIG. 1, which has been constructed in a manner that is consistent with one or more embodiments of the invention. As shown, the liner 112 is constructed as a unitary structure of tissue in-growth material. The intermediate portion 114 of the liner 112 includes a reinforcing structure 116 (shown as a coil 118) while the proximal and distal portions 120, 122 do not include the reinforcing structure 116. As shown in phantom, the inflow cannula 58 may also include one or more longitudinal strengtheners 124 that extend, at least partially along the intermediate portion 114 between the liner 112 and the reinforcing structure 116, if present, and/or the jacket 126. The longitudinal strengtheners 124, in addition to the reinforcing structure 116, provide better longitudinal control over the length of the inflow cannula 58. Any semi-flexible or flexible material may be used for constructing the longitudinal strengtheners 124, including for example, non-absorbable suture materials such as nylon or polypropylene; however, metallic materials, alloys, and/or other materials may also be used.

As is shown in FIG. 3, the tip 60 may be constructed from a polished titanium or other suitable material and have a design that reduces fluidic turbulence and the risk of thrombosis formation. The tip design may also facilitate the coupling of the tip 60 to the distal portion 122 of the liner 112 of the inflow cannula 58. For example, in some embodiments, a proximal end of the tip 60 may include one or more barbs 128 to provide resistance against undesired removal of the tip 60 from the inflow cannula 58. The tip 60 may additionally, or alternatively, be coupled and/or secured to the inflow cannula 58 by a suture tie 130 (FIG. 5A) that is encapsulated by a UV adhesive 132 (FIG. 5A), which is cured in a known manner. The suture tie 130 is operable to cinch and secure the inflow cannula 58 onto the tip 60. In yet other embodiments, the tip 60 may be additionally, or alternatively, secured to the inflow cannula 58 by a band 134 (FIG. 5B) that is operable to swage or crimp the cannula 58 onto the tip 60. Optionally, the band 134 (FIG. 5B) may be constructed from a material that would enable a surgeon to remotely determine the location of the tip 60, including but not limited to radiopaque materials, such as platinum-iridium, stainless steel, tungsten, or tantalum. Such remote visualization may be accomplished in any known manner, such as real time fluoroscopy or ultrasonography. The band 134 (FIG. 5B) may be further covered or encapsulated with a cover 136 that is constructed of the tissue in-growth material, consistent with any of the embodiments described herein.

The proximal end of the inflow cannula 58 may be expanded to form a hub 138 that is configured to be coupled to the inflow port 64 (FIG. 1) of the pump 50 (FIG. 1).

The inflow cannula construction with the tissue in-growth material allows for the attachment of endothelial cells from the blood flowing through the lumen 90. Once the endothelial cells attach, they may undergo mitosis and proliferate to cover the length of the liner 112 that is constructed from the tissue in-growth material. This endothelial cell growth creates a biostable layer that more accurately replicates the native environment of a blood vessel. With the biostable layer, there is a reduction in perturbations that would induce endothelial generation of a prothrombotic environment. Accordingly, there is a reduction of thrombus formations that in return decreases the occurrence of pump failures.

Figure 3A:
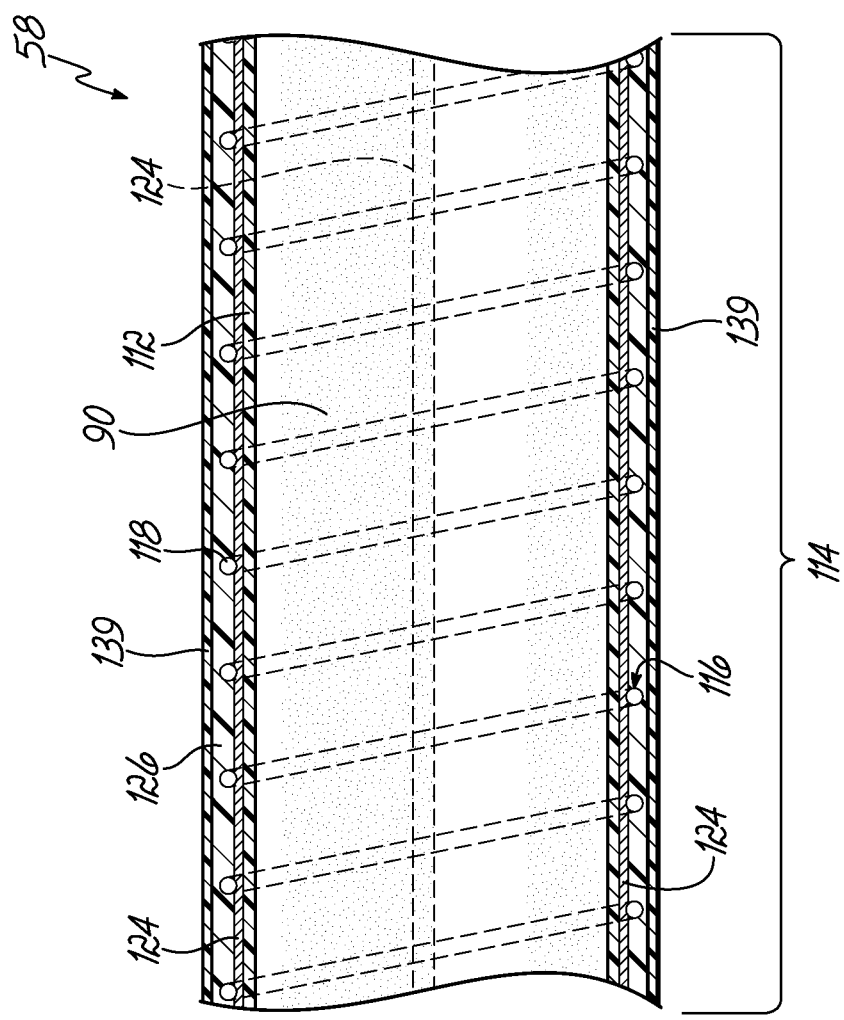
FIG. 3A is an enlarged and fragmented view of another embodiment of an inflow cannula, shown in cross-section.

FIG. 3A illustrates an alternate embodiment of the inflow cannula 58. More specifically, an outer layer 139 constructed from a tissue in-growth material is added to the outer surface of the jacket 126. The tissue in-growth material may be a porous polymeric material, such as expanded ePTFE, a woven polyester fabric tubing (e.g., DACRON brand of polyester fabric), velour, or like materials that create a scaffolding to which cells adhere. The outer layer 139 extends over at least the intermediate portion 114 of the inflow cannula 58, but may also extend over the distal and proximal portions 122, 120, if desired. Inclusion of this outer layer 139 is useful when the inflow cannula 58 resides within the vascular network, for example as shown in FIG. 1, and particularly where blood flow may stagnate due to the inflow cannula 58. As the inflow cannula 58 extends through the right subclavian vein 26 (FIG. 1) and the superior vena cava 32 (FIG. 1) as shown in FIG. 1, there may be a tendency for the inflow cannula 58 to contact an inner surface of the venous wall, particularly along curving portions of the walls. Those areas in which the inflow cannula 58 contacts the venous wall will experience reduced blood flow, i.e., stagnation, which may then lead to thrombus formation. By including the tissue in-growth material as the outer layer 139 to the inflow cannula 58, a biostable environment is created that replicates the vascular environment and reduces perturbations that would otherwise generate a prothrombotic environment. While the outer layer 139 is illustrated here with the inflow cannula, it would be readily appreciated that the outer layer 139 may be included on one or more portions of the outflow cannula 74 (FIG. 1) if desired.

The inflow cannula 58 may be delivered in a surgical method, such as those described in U.S. patent application Ser. No. 11/846,839, or in a percutaneous manner, such as described in U.S. patent application Ser. No. 12/256,911. Percutaneous delivery may proceed by way of a delivery system 140, which is illustrated in FIG. 4A. The delivery system 140 includes a delivery sheath 142 having a body 144 that may be constructed as three thin-layer walls, though it is illustrated as a single-walled structure herein. An exterior layer may be constructed of polyurethane, Nylon-11, Nylon-12, or PEBAX; an interior layer can be a liner made from an ePTFE, urethane, or Nylon with hydrogel coating; and a mid-layer can be constructed from a braided material, such as stainless steel wire, Nitinol, or polyetheretherketones (PEEK) fibers to provide structural stability to the delivery sheath 142. The interior layer or an interior liner may be extruded and placed upon a mandrel with the mid-layer and the exterior layer respectively formed or otherwise placed over the interior layer. Polyurethane is then placed over the entire assembly and heat shrink wrapped over the tube for stability. Alternatively, the delivery sheath 142 may be laminated by a reflow process. In some instances, a superelastic coil (not shown) may be included around the delivery sheath 142 to increase the rigidity of the delivery sheath 142. Alternatively, a metallic braid (not shown) could be included around the delivery sheath 142. A polymeric layer may surround the superelastic coil (not shown) to reduce friction as the delivery sheath 142 moves within the vascular network.

A distal end of the delivery sheath 142 may include a balloon-expandable section 146, which may be a multilayer construction having two states: a first, non-expanded state (shown in FIG. 4B) and a second, expanded state (shown in FIG. 4A). The multilayer construction may be formed from lower durometer materials such as PEBAX brand of polymers or polyurethane for compliant or easy inflation or from higher durometer materials such as nylon or polyethylene terephthalate (PET) for a balloon-expandable section 146 that is more resistant to inflation. As an alternate configuration, the balloon expandable section 146 may be constructed using a porous polymeric material such as ePTFE, DACRON brand of polyester fabrics, or velour, as the inner and outer layers with a balloon expandable structure 148 sandwiched between the layers. The balloon expandable structure 148 may reside between the inner layer and the outer jacket in a manner that may be similar to a covered stent-like construction and may be constructed from a deformable material, such as a metallic alloy (e.g., stainless steel, or chromium cobalt, CrCo) or a rigid polymer, that aids in preventing the collapse of the delivery sheath 142 due to tissue recoil during insertion of the inflow cannula 58 (FIG. 1). One suitable balloon expandable structure 148 may be machined from a hypo-tube in a manner that is similar to the construction of a balloon-expandable stent. When the proximal support structure is used, the proximal section of the balloon expandable structure 148 may be coupled to the distal end of the superelastic coil (not shown).

A hub 150 is attached to a proximal end of the delivery sheath 142 by gluing, welding, or other means. The hub 150 may include a side port 152 having a conduit 154 that extends to a flush valve 156. Though not specifically shown, the hub 150 may include any suitable hemostatic seal for preventing the back-flow of bodily fluid and should not be limited to the structure illustrated herein.

A dilator 158, specifically illustrated as a balloon appliance, is backloaded through the hub 150 and into a lumen of the delivery sheath 142 to the balloon-expandable section 146 while an expandable portion 162 of the dilator 158 is in a deflated state. The dilator 158 may be any commercially-available balloon catheter and generally includes a catheter body 160 and an expandable distal portion 162, illustrated specifically herein as a balloon 164. In some embodiments, the length of the balloon 164 would be substantially similar to the length of the balloon-expandable section 146 of the delivery sheath 142 so that the balloon 164 need only be inflated once; however, in other embodiments where the length of the balloon-expandable section 146 exceeds the length of the balloon 164, then multiple inflations/deflations may be necessary to ensure that the entire length of the balloon-expandable section 146 is fully expanded. Further, it would be understood that when the expanded diameter of the balloon 164 substantially matches the desired expanded diameter of the balloon-expandable section 146, then full inflation of the balloon 164 would result in the desired diameter of the balloon-expandable section 146; however, embodiments where partial inflation of a balloon 164 having a diameter that is greater than the desired expanded diameter of the balloon-expandable section 146 would also be acceptable.

The catheter body 160 and a proximally-positioned hub 166 (for example, a "Y"-shaped hub) may include a multi-lumen tube or multiple tubes such that one tube or lumen receives a guidewire 168 and another tube or lumen facilitates inflation/deflation of the balloon 164. In some embodiments, though not shown, a needle (for example, a transseptal needle) may be used in place of, or in addition to, the guidewire 168. Accordingly, the needle may include a hub configured to receive the guidewire 168.

The assembled delivery system 140, including the guidewire 168, is shown in FIG. 4B such that the dilator 158 extends through the lumen of the delivery sheath 142 and the balloon-expandable section 146. The balloon-expandable section 146 is compressed, typically by crimping, onto the balloon 164 while in its non-expanded, or collapsed, state.

Figure 4E:
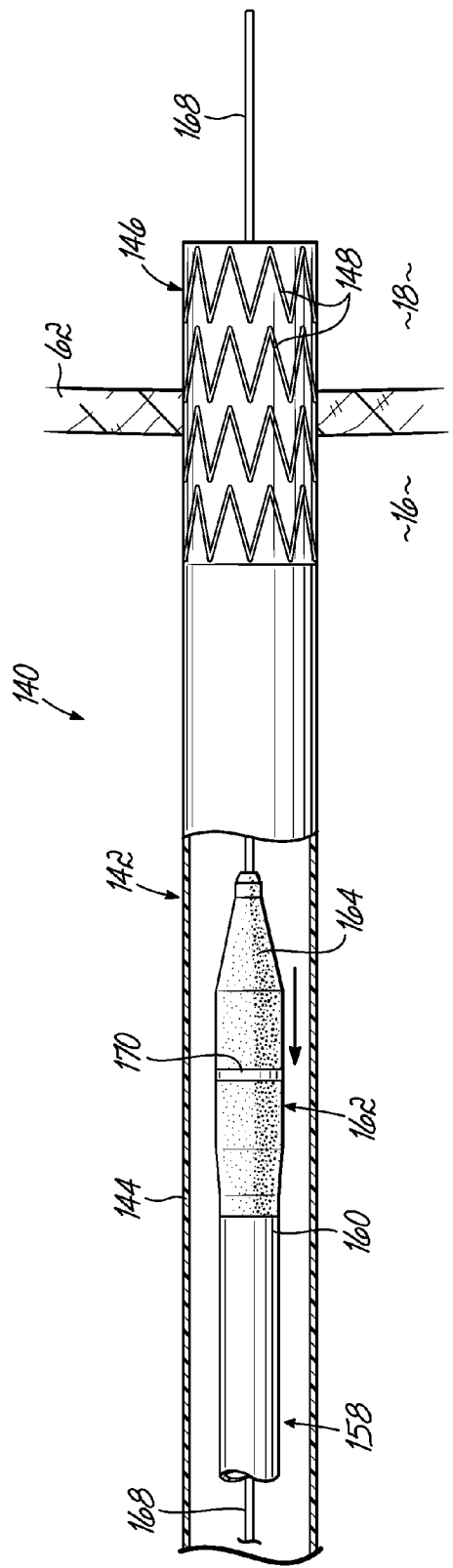

Use of the delivery system 140 may proceed, as illustrated in FIGS. 4C-4E with reference also to FIG. 1, by advancing the guidewire 168 to the surgical site for implanting the inflow cannula 58. In the particular illustrative embodiment, the guidewire 168 may be inserted through the venous access site 56 at the right subclavian vein 26 and advanced through the superior vena cava 32 and into the right atrium 16. From the right atrium 16, the guidewire 168 may puncture the intra-atrial septum 62 and enter the volume of the left atrium 18. While not shown, it would be readily understood that the procedure may also proceed by way of the transseptal needle, described previously, that is then exchanged with the guidewire 168.

The delivery sheath 142 with the dilator 158 may then be advanced over the guidewire 168 and to the right atrial side of the intra-atrial septum 62. Because the balloon-expandable section 146 of the delivery sheath 142 and the balloon 164 are both collapsed, and thereby have a small profile, the delivery system 140 may advance over the guidewire 168, through the puncture in the intra-atrial septum 62, and into the left atrium 18. The tapered shape of the balloon-expandable section 146 dilates the puncture and facilitates insertion of the delivery sheath 142 through the intra-atrial septum 62. Positioning of the delivery system 140 with respect to the intra-atrial septum 62 may be facilitated by in vivo localization of one or more marker bands 170 that are positioned on the dilator 158 (refer to FIG. 4E), and that are constructed from a radiopaque material and visualized as described above.

As shown in FIG. 4D, with the delivery sheath 142 inserted through the intra-atrial septum 62, the balloon 164 of the dilator 158 may be inflated, in a known manner, causing expansion of the balloon 164 against an inner surface of the balloon-expandable section 146 of the delivery sheath 142. The balloon-expandable section 146 also expands, thereby further dilating the puncture.

FIG. 4E illustrates the deflation and retraction of the balloon 164 after one or more inflation/deflation steps ensure full expansion of the balloon-expandable section 146. The balloon-expandable section 146 retains its fully expanded state and resists recoil of the tissue during passage of the inflow cannula 58.

Figure 4F:
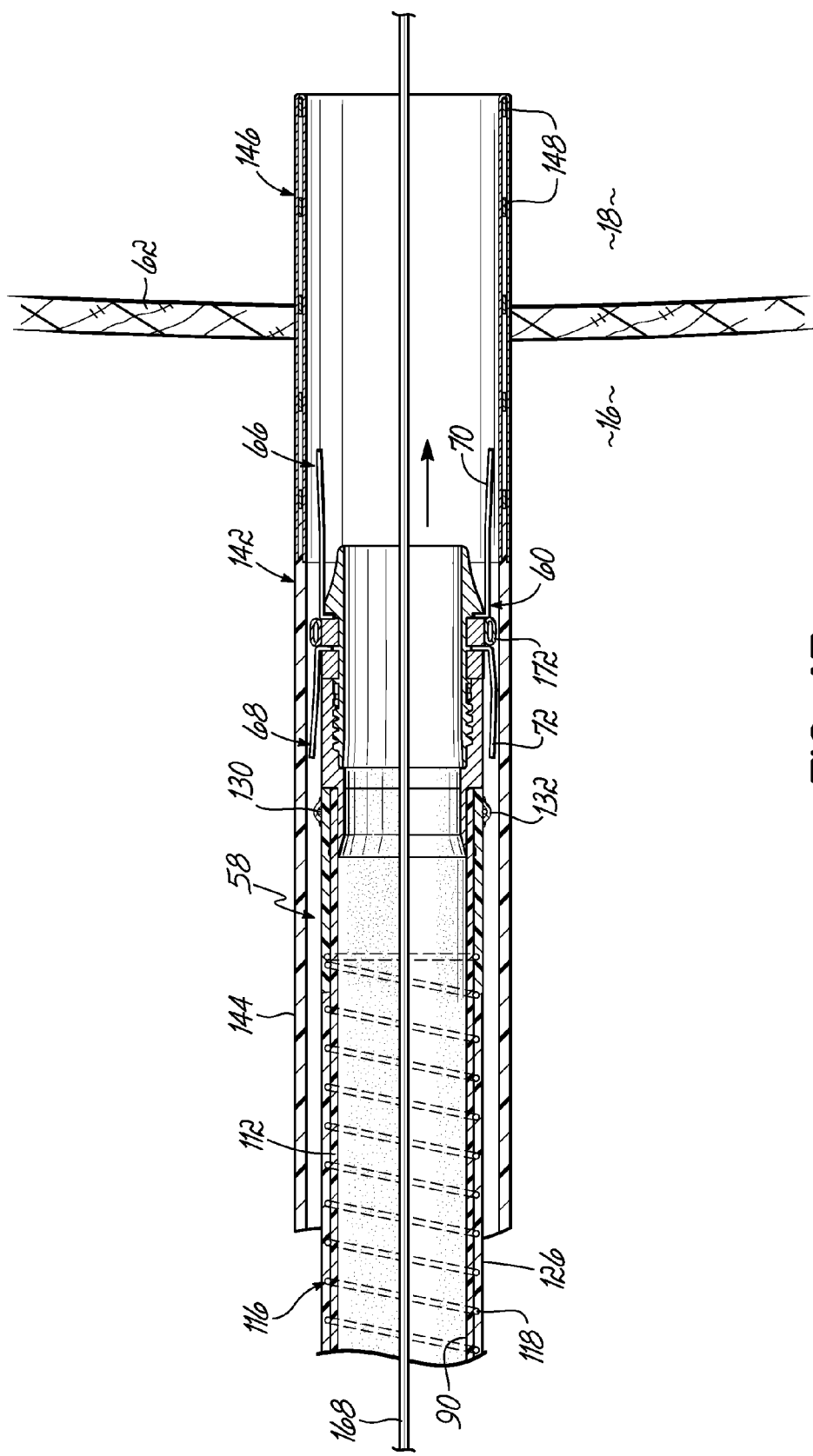
FIG. 4F is an enlarged, cross-sectional view of an exemplary method of advancing an inflow cannula through the delivery sheath positioned through the tissue wall.

FIG. 4F illustrates the inflow cannula 58, which is advanced through the lumen of the delivery sheath 142 to the intra-atrial septum 62. Deployment of the anchors 66, 68 on the tip 60 may proceed in the manner that was described in detail in U.S. patent application Ser. No. 12/256,911. Briefly, the inflow cannula 58 with the tip 60 is advanced beyond the balloon-expandable section 146 of the delivery sheath 142 and into the volume of the left atrium 18 such that the first anchor 66, unrestrained by the delivery sheath 142, is deployed and expands radially outward. The delivery sheath 142 with the inflow cannula 58 are retracted such that the first anchor 66 resides adjacent the intra-atrial septum 62 within the left atrium 18. While maintaining the position of the inflow cannula 58, the delivery sheath 142 is then further retracted, thereby deploying the second anchor 68 on the right atrial side of the intra-atrial septum 62, such that the tip 60 spans the intra-atrial septum 62, and the anchors 66, 68 reside on opposing sides of the intra-atrial septum 62, as shown in FIG. 1.

Figure 5A:
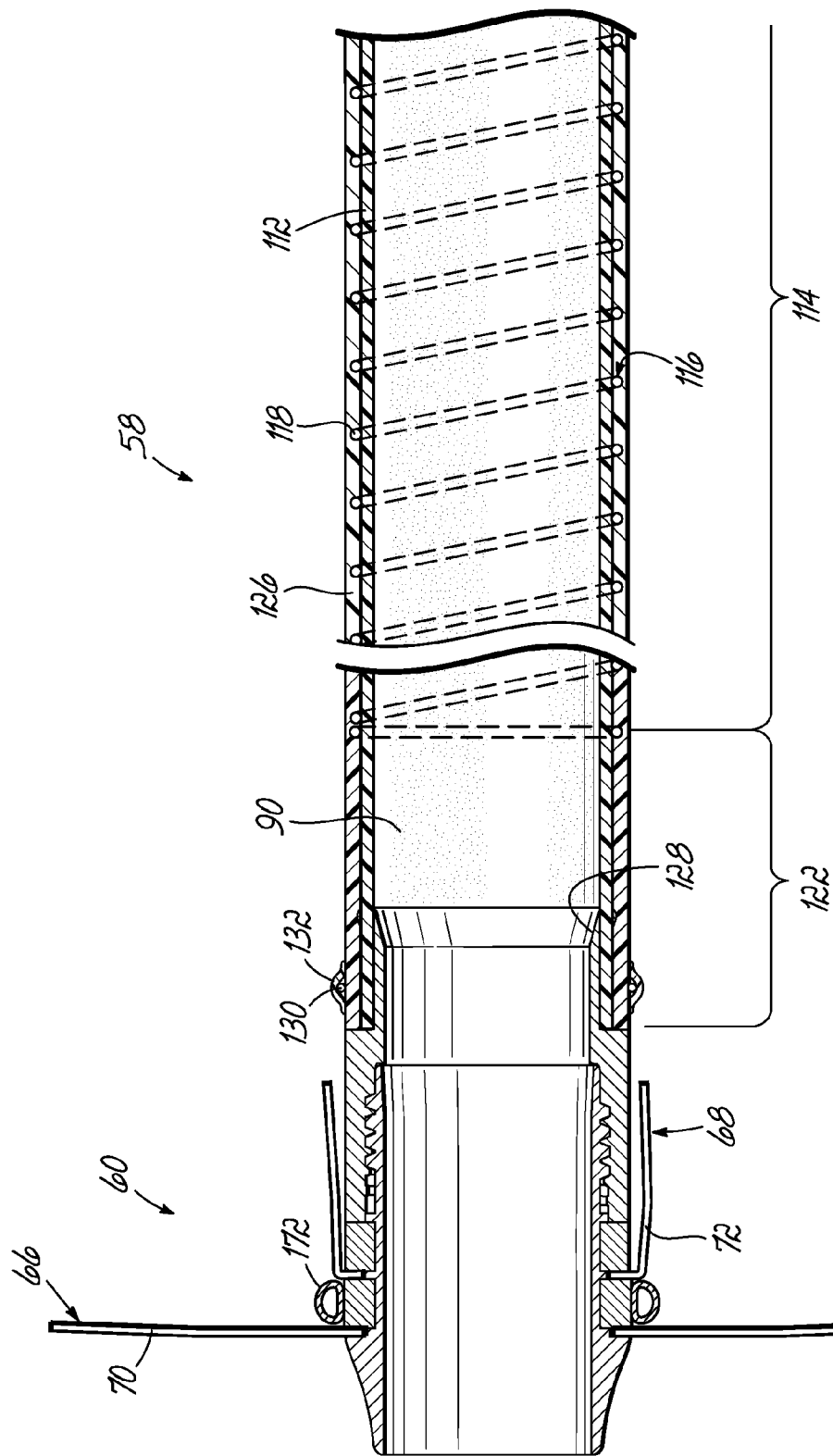
FIG. 5A is a cross-sectional view of another embodiment of an inflow cannula having a tip coupled to the distal end thereof.
Figure 5B:
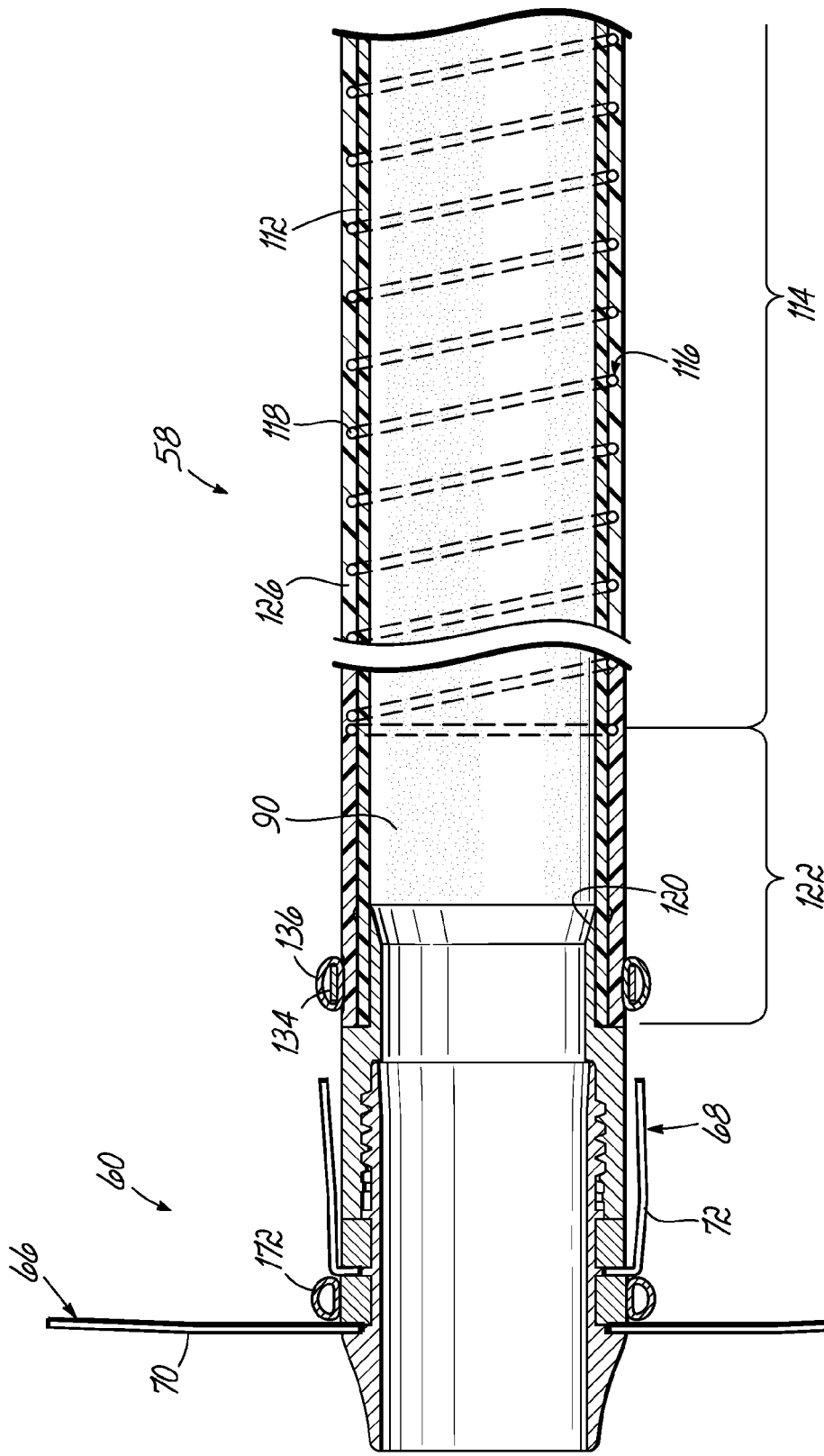
FIG. 5B is a cross-sectional view of yet another embodiment of an inflow cannula having a tip coupled to the distal end thereof.

The inflow cannula 58, illustrated with greater detail in FIGS. 5A and 5B, includes a tissue in-growth member, such as a band 172. While the band 172 covers only a portion of an outer surface of the tip 60, other forms of tissue in-growth members may be used instead, and may cover the entire outer surface of the tip 60. The band 172 is annular and resides along the circumferential surface between the first and second anchors 66, 68. The band 172 may be formed of any suitable material that promotes tissue in-growth, such as any of the materials discussed herein for that purpose. In some embodiments, it may be beneficial to increase the distance between the first and second anchors 66, 68 to accommodate the band 172. After the tip 60 is secured to the intra-atrial septum 62 (FIG. 1), tissue of the septum 62 (FIG. 1) may at least partially grow into the material comprising the band 172, further securing the tip 60 to the septum 62 (FIG. 1). In yet other embodiments, the material comprising the band 172 may include a coating or otherwise be infused with a material that promotes healing of the tissue comprising the intra-atrial septum 62 (FIG. 1) at the surgical site. The coating may include a prothrombotic coating or a coating of calcium phosphate ($Ca_3(PO_4)_2$) to further promote tissue in-growth.

Turning now to FIG. 6A, the outflow cannula 74 of FIG. 1, which has been constructed in a manner that is consistent with one or more embodiments of the invention, is described in greater detail. While the liner 176 of the outflow cannula 74 is illustrated as a unitary structure, this is not necessary. The intermediate portion 178 of the liner 176 includes the braid 108 as the reinforcing structure 180 for kink resistance; however, a coil 106 (FIG. 2) or other suitable structure may alternatively be used. Furthermore, the reinforcing structure 180, as illustrated, does not extend over the proximal and distal portions 182, 184 to maintain flexibility of these portions; however, this should not be considered necessary.

The distal portion 184 of the liner 176 extends distally beyond the jacket 186 and is constructed from a thicker walled of material such that the outer diameter of the liner 176 at the distal portion 184 is substantially similar to the outer diameter of the outflow cannula 74 at the jacket 186 and forms a protruding section 188. In this way, the protruding section 188 may be used to create an anastomosis connection with the arterial structure, shown herein as the right subclavian artery 46 (FIG. 1); however, it would be understood by one skilled in the art that the protruding section 188 is not necessary and that a tip with an anchor, a suture, or other means may be used for attaching the outflow cannula 74 to the arterial structure.

The proximal end of the outflow cannula 74 may be expanded to form a hub 190 that is configured to be coupled to the outflow port 76 (FIG. 1) of the pump 50 (FIG. 1).

The outflow cannula construction with the tissue in-growth material allows for the attachment of endothelial cells from the blood flowing through a lumen 192 of the outflow cannula 74. Again, once the endothelial cells attach, undergo mitosis, and proliferate to cover the length of the liner 176 constructed from the tissue in-growth material, a biostable layer is created that more accurately replicates the native environment of a blood vessel. With the biostable layer, there is a reduction in perturbations that would induce endothelial generation of a prothrombotic environment. Accordingly, there is a reduction of thrombus formations leading to decreases in the occurrence of outflow-cannula-induced thrombolic events, i.e., kidney infarct and/or stroke.

FIG. 6B illustrates an alternate embodiment of an outflow cannula 194 having a liner 196 that includes a tapered diameter such that the proximal portion 198 of the liner 196 has a lumen of a first diameter, D1, that is generally larger than the lumen of a second diameter, D2, of the distal portion 200 of the liner 196. This configuration is particularly beneficial when a larger diameter is required for attachment to the pump 50 (FIG. 1) and a smaller diameter is desired at the vessel. As illustrated herein, the smaller diameter distal portion 200 is constructed as a protruding section 202 that is similar to the construction described above. As shown in the instant embodiment, the protruding section 202 need not be constructed to match the outer diameter of the outflow cannula 194 at the jacket 204 but, instead, may maintain the tapering diameter for the length of the outflow cannula 194.

The tapered cannula 194 may have a D1 that ranges from about 6 mm to about 10 mm and a D2 that ranges from about 3 mm to about 7 mm. Also, while the outflow cannula 194 has been shown herein as including a taper that extends over the full length of the outflow cannula 194, other configurations may also be used, for example, a taper that extends only between the intermediate portion 206 and the distal portion 200.

As noted above, the outflow cannula 194 may include a reinforcing structure 210, shown as a coil, over at least the intermediate portion 206 of the liner 196. The proximal end of the outflow cannula 194 may also be expanded to form a hub 212.

Returning now to FIG. 1, once the cannulae 58, 74 are positioned and coupled to the pump 50, the circulatory assist system 10 may be used to aid the heart 12 in pumping the patient's blood through the vascular network. Depending on the cardiac output of the patient 14, a portion of blood flow will proceed in the native manner with oxygenated blood traveling from the left atrium 18 into the left ventricle 22 to the aorta 38. From the aorta 38, blood moves into the left subclavian artery 40, the left common carotid 42, and the brachiocephalic trunk 44. Another portion of the blood flow will proceed along the artificial path by entering the inflow cannula 58 and traveling through the lumen 90 (FIG. 3) of the inflow cannula 58 to the pump 50. From the pump 50, blood flows through the outflow cannula 74 to the particular arterial structure, here, the right subclavian artery 46.

Other cannulae in accordance with other embodiments of the invention are shown in FIGS. 7-10. In FIG. 7, the cannula 220 includes a liner 222 constructed from a tissue in-growth material as described above. The liner 222 includes an intermediate portion 224 with a first outer diameter, d1, and distal and proximal portions 226, 228, each with a second outer diameter, d2, where d2 is greater than d1. The outer surface may taper, as shown, from d2 to d1. The smaller, outer diameter, d1, provides a channel in which the reinforcing structure 230 (illustrated as a coil but may alternatively be a braid or other structure) resides. An intermediate polymeric layer 232 is applied over the reinforcing structure 230 and has a thickness that is sufficient to increase the outer diameter, d1, at the intermediate portion 224 to be approximately similar to the diameter d2 at the distal and proximal portions 226, 228. The intermediate polymeric layer 232 may be constructed from a thermoplastic or thermoset material, such as urethane or silicone or other similar material.

The liner 222 and the intermediate polymeric layer 232 are covered with a jacket 234, which, may be constructed and applied as described previously. In another embodiment, the jacket 234 may be an extruded tube that is placed over the liner 222 and the intermediate polymeric layer 232. In yet other embodiments, the jacket 234 may be formed by a dip process. That is, the cannula 220 may be dipped into a dilute polymer solution that, when dry, forms a layer of the polymer on the cannula 220. Exemplary materials for the polymer solution may include, for example, polyurethane pellets or a silicone emulsion.

The cannula 240 illustrated in FIG. 8 is similar to the cannula 220 of FIG. 7. However, in FIG. 8, the outer diameter of the liner 242 expands from d1 at the intermediate portion 244 to a third diameter, d3, at both the proximal and distal portions 246, 248. The third diameter, d3, is greater than d1 and, in the instant embodiment, d3 is equivalent to the outer diameter of the cannula 240. The outer diameter is shown to slope, or taper, between d1 and d3, although this is not required. Again, the larger, outer diameter, d3, of the proximal and distal portions 246, 248 define a channel at the intermediate portion 244 in which the reinforcing structure 250, the intermediate polymeric layer 252, and the jacket 254 are layered. The layering is sufficient to increase the outer diameter of the cannula 240 at the intermediate portion 244 to be approximately similar to d3. The final cannula structure includes tissue in-growth material extending along the lumen 256 and at least the proximal and distal outer ends 258, 260 of the cannula 240. The structure allows cellular growth on both the inside and outside of the cannula 240 to support the formation of a biostable layer and to replicate the native environment of a blood vessel.

With reference now to FIG. 9, a cannula 266 in accordance with yet another embodiment of the invention is described. The cannula 266 is constructed in a manner that is similar to the inflow cannula 92 of FIG. 2. Specifically, the cannula 266 includes a liner 268 having a unitary construction and with a substantially uniform inner diameter between the proximal, intermediate, and distal portions 270, 272, 274. A reinforcing structure 276 surrounds at least the intermediate portion 272 of the liner 268. Both the liner 268 and the reinforcing structure 276 are encapsulated by a first polymeric layer 278, which may be similar in construction to the jacket 110 of FIG. 2. The cannula 266 further includes a tissue in-growth layer 280 that is applied onto the first polymeric layer 278 and extends over at least the intermediate portion 272 of the liner 268. Alternatively, the tissue in-growth layer 280 may extend the full length of the cannula 266, such as was described with the outer layer 139 of FIG. 3A.

To prevent delamination of the tissue in-growth layer 280 from the first polymeric layer 278, a second polymeric layer 282 may be applied to the proximal and distal portions 270, 274. For example, the second polymeric layer 282 may include a first portion 283 extending proximally from the proximal end 288 of the tissue in-growth layer 280, e.g., to the proximal end 284 of the cannula 266 and capturing the proximal end 288 of the tissue in-growth layer 280. A second portion 285 of the second polymeric layer 282 extends distally from the distal end 290 of the tissue in-growth layer 280, e.g., to the distal end 286 of the cannula 266 and captures the distal end 290 of the tissue in-growth layer 280. While not required, the first and second polymeric layers 278, 282 may be constructed of the same material.

Again, the result is a cannula 266 that is configured to create a biostable environment along its inner diameter and at least a portion of its outer diameter.

One unexpected benefit of cannulae incorporating a tissue in-growth layer construction is that the elongation characteristics of the cannula are limited. More specifically, during manipulation of some conventional cannulae, the cannula may be inadvertently stretched by the physician, which results in damage to the cannula, such as by tearing. Tearing is also possible during the manipulation of the cannula relative to a delivery sheath during insertion or relative to a deployment device during recapture and/or removal of the cannula. Cannula stretching also reduces the 1:1 ratio between what the physician feels when percutaneously maneuvering the cannula and what the physician observes on either fluoroscopy or ultrasonography. A direct correlation between movement and visualization is necessary for the physician to accurately and safely perform the percutaneous procedures. Therefore, while not every cannula requires a biostable surface, cannulae for percutaneous procedures, generally, would benefit from limited elongation characteristics.

One such cannula 294 is illustrated in FIG. 10 and includes a porous polymeric layer 296 that is captured between inner and outer polymeric layers 298, 300. The materials comprising the porous polymeric layer 296 may be similar to the tissue in-growth materials described previously and the polymeric layers 298, 300 may be constructed from materials described previously with respect to the polymeric jacket materials. A reinforcing structure 302, including a braid, a coil, or other structure may be included, if desired, between the porous polymeric layer 296 and either of the inner or outer polymeric layers 298, 300, though only the former is shown herein. While the cannula 294 does not support tissue growth on either of the inner or outer diameters, inclusion of the tissue in-growth material does limit the elongation characteristics and facilitates the 1:1 response.

While the present invention has been illustrated by a description of various preferred embodiments and while these embodiments have been described in some detail, it is not the intention of the Applicants to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with the preferred methods of practicing the present invention as currently known. However, the invention itself should only be defined by the appended claims.

What is claimed is:

1. A cannula for moving blood between a pump and a circulatory system of a patient, the cannula comprising:
    a liner comprising an intermediate portion between a proximal portion and a distal portion and a lumen extending between the proximal and distal portions, wherein at least the intermediate portion is constructed from tissue in-growth material adapted to contact blood flowing through the lumen for supporting the growth of endothelial cells, the proximal portion is configured for connecting to the pump and the distal portion is configured for connecting to the circulatory system;
    a jacket fully encapsulating the liner;
    an outer layer surrounding at least a part of the jacket;
    wherein the outer layer has a proximal and a distal end and an intermediate portion therebetween; and
    a polymeric layer extending along a partial length of the liner and the outer layer, the polymeric layer having a first portion that extends proximally from the proximal end of the outer layer to a proximal end of the cannula and a second portion that extends distally from the distal end of the outer layer to the distal end of the cannula such that the first and second portions of the polymeric layer prevent delamination of the outer layer from the jacket, the first and second portions of the polymeric layer further encapsulating the proximal and distal portions of the jacket without encapsulating the intermediate portion of the outer layer.

2. The cannula of claim 1, wherein the tissue in-growth material is an expanded polytetrafluoroethylene, a porous polymeric material, a woven polyester material, or a velour.

3. The cannula of claim 1, wherein the proximal and distal portions of the liner are constructed from an elastomeric material.

4. The cannula of claim 1, wherein the jacket is constructed from a polymeric material and is bonded to the liner.

5. The cannula of claim 1, wherein the distal portion is constructed from the tissue in-growth material.

6. The cannula of claim 1, wherein the liner is constructed as a unitary structure having the distal, intermediate, and proximal portions constructed from the tissue in-growth material.

7. The cannula of claim 1 further comprising:
a reinforcing structure surrounding at least a part of the intermediate portion of the liner for resisting kinks along the length of the cannula, wherein the liner and the jacket encapsulate the reinforcing structure.

8. The cannula of claim 1, further comprising:
one or more longitudinal strengtheners positioned between the liner and the jacket, and extending at least partially between the proximal and distal portions.

9. The cannula of claim 1, wherein the outer layer is bonded to the jacket.

10. A cannula for moving blood between a pump and the circulatory system of a patient, the cannula comprising:
a liner comprising an intermediate portion between a proximal portion and a distal portion and a lumen extending between the proximal and distal portions, wherein at least the intermediate portion is constructed from tissue in-growth material adapted to contact blood flowing through the lumen for supporting the growth of endothelial cells, the proximal portion is configured for connecting to the pump and the distal portion is configured for connecting to the circulatory system;
a reinforcing structure surrounding at least a part of the intermediate portion of the liner for resisting kinks along the length of the cannula;
a jacket surrounding the reinforcing structure and fully encapsulating the liner;
an outer layer surrounding at least a part of the jacket, the outer layer including a proximal and a distal end and an intermediate portion therebetween; and
a polymeric layer extending along a partial length of the liner and the outer layer, the polymeric layer having a first portion that extends proximally from the proximal end of the outer layer to a proximal end of the cannula and a second portion that extends distally from the distal end of the outer layer to the distal end of the cannula such that the first and second portions of the polymeric layer prevent delamination of the outer layer from the jacket, the first and second portions of the polymeric layer further encapsulating the proximal and distal portions of the jacket without encapsulating the intermediate portion of the outer layer.

11. The cannula of claim 10, wherein the tissue in-growth material is a porous polymeric material, a woven polyester material, expanded polytetrafluoroethylene, or a velour.

12. The cannula of claim 10, wherein the liner is constructed as a unitary structure having the distal, intermediate, and proximal portions constructed from the tissue in-growth material.

13. The cannula of claim 10, wherein the jacket is constructed from a polymeric material and is bonded to the liner.

14. The cannula of claim 10, wherein the jacket fully encapsulates the proximal and distal portions of the liner.

15. The cannula of claim 10, wherein the outer layer is bonded to the jacket.

16. An inflow cannula for moving blood from the heart of a patient to a pump, the inflow cannula comprising:
a liner comprising an intermediate portion between a proximal portion and a distal portion and a lumen extending between the proximal and distal portions, wherein at least the intermediate portion is constructed from tissue in-growth material adapted to contact blood flowing through the lumen for supporting the growth of endothelial cells;
the distal and proximal portions of the liner have respective outer diameters that are greater than an outer diameter of the intermediate portion of the liner so as to define a channel at the intermediate portion, the channel having an outer diameter that is less than the outer diameter of the distal and proximal portions;
an intermediate polymeric layer disposed in the channel;
a jacket fully encapsulating the intermediate polymeric layer;
a tip coupled to the distal portion and configured to be inserted through a wall of the heart; and
a hub coupled to the proximal portion and configured to secure the inflow cannula to the pump.

17. The cannula of claim 16, further comprising:
a reinforcement structure positioned in the channel between the liner and the intermediate polymeric layer so as to form a layering of the liner, the reinforcement structure, the intermediate polymeric layer, and the jacket.

18. An outflow cannula for moving blood from a pump to the circulatory system of a patient, the outflow cannula comprising:
a liner comprising an intermediate portion between a proximal portion and a distal portion and a lumen extending between the proximal and distal portions, wherein at least the intermediate portion is constructed from tissue in-growth material adapted to contact blood flowing through the lumen for supporting the growth of endothelial cells;
the distal and proximal portions of the liner have respective outer diameters that are greater than an outer diameter of the intermediate portion of the liner so as to define a channel at the intermediate portion, the channel having an outer diameter that is less than the outer diameter of the distal and proximal portions;
an intermediate polymeric layer disposed in the channel;
a jacket fully encapsulating the intermediate polymeric layer;
a hub coupled to the proximal portion and configured to secure the outflow cannula to the pump;
and a distal end that is configured to be coupled to the circulatory system.

19. The cannula of claim 18, further comprising:
a reinforcement structure positioned in the channel between the liner and the intermediate polymeric layer so as to form a layering of the liner, the reinforcement structure, the intermediate polymeric layer, and the jacket.

20. A cannula for moving blood between a pump and a circulatory system of a patient, the cannula comprising:
a liner comprising a proximal portion, a distal portion, an intermediate portion located between the proximal and distal portions, and a lumen extending between the proximal and distal portions, wherein at least the intermediate portion is constructed from tissue in-growth material adapted to contact blood flowing through the lumen for supporting the growth of endothelial cells, the proximal portion is configured for connecting to the pump and the distal portion is configured for connecting to the circulatory system;

a jacket fully encapsulating the liner;
wherein the distal and proximal portions each have an outer diameter that is greater than an outer diameter of the intermediate portion of the liner so as to define a channel at the intermediate portion; and an intermediate polymeric layer disposed in the channel; and
an intermediate polymeric layer disposed in the channel and fully encapsulated by the jacket.

21. The cannula of claim 20, further comprising:
a reinforcement structure positioned in the channel between the liner and the intermediate polymeric layer so as to form a layering of the liner, the reinforcement structure, the intermediate polymeric layer, and the jacket.

\* \* \* \* \*